United States Patent
Lichtsteiner et al.

(10) Patent No.: US 10,550,378 B2
(45) Date of Patent: *Feb. 4, 2020

(54) COMPOSITION COMPRISING A GENE VECTOR THAT SELECTIVELY DEPLETES P16 POSITIVE SENESCENT CELLS

(71) Applicants: Unity Biotechnology, Inc., Brisbane, CA (US); Kythera Biopharmaceuticals, Inc., Calabasas, CA (US)

(72) Inventors: Serge Lichtsteiner, Westlake, CA (US); Nathaniel David, Brisbane, CA (US)

(73) Assignees: Unity Biotechnology, Inc., Brisbane, CA (US); Kythera Biopharmaceuticals, Inc., Calabasas, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/436,265

(22) Filed: Jun. 10, 2019

(65) Prior Publication Data

US 2019/0316109 A1  Oct. 17, 2019

Related U.S. Application Data

(60) Continuation of application No. 16/029,244, filed on Jul. 6, 2018, now Pat. No. 10,378,002, which is a division of application No. 14/394,854, filed as application No. PCT/US2013/036811 on Apr. 16, 2013, now abandoned.

(60) Provisional application No. 61/625,612, filed on Apr. 17, 2012.

(51) Int. Cl.
| | | |
|---|---|---|
| *C12N 9/50* | (2006.01) | |
| *A61K 38/48* | (2006.01) | |
| *C12N 15/85* | (2006.01) | |

(52) U.S. Cl.
CPC ............ *C12N 9/50* (2013.01); *A61K 38/4873* (2013.01); *C12N 15/85* (2013.01); *C12N 2740/10043* (2013.01); *C12N 2740/15043* (2013.01); *C12Y 304/22* (2013.01)

(58) Field of Classification Search
CPC ....................................................... C12N 9/50
See application file for complete search history.

(56) References Cited

U.S. PATENT DOCUMENTS

2010/0028302 A1*  2/2010  Hoflich .............. A01K 67/0275
                                                    424/93.2

OTHER PUBLICATIONS

Baker et al. ("Clearance of p16Ink4a-positive senescent cells delays ageing-associated disorders", Nature, Nov. 10, 2011, vol. 479, No. 7372, Nov. 2, 2011, pp. 232-236) (Year: 2011).*
Yao et al (Human Gene Therapy. Feb. 1, 1999; 10(3): 419-427) (Year: 1999).*

* cited by examiner

*Primary Examiner* — Scott Long
(74) *Attorney, Agent, or Firm* — Janet Martineau; Wilson Sonsini Goodrich & Rosati

(57) ABSTRACT

Polypeptides, viruses, methods and compositions provided herein are useful for the selective elimination of senescent cells. Method aspects include methods for inducing apoptosis in a senescent cell comprising administering to the cell a polynucleotide, virus, host cell, or pharmaceutical composition described herein. Other methods include expressing a pro-apoptotic gene in a senescent cell comprising administering to the cell the polynucleotide, virus, or pharmaceutical composition as described herein.

10 Claims, 4 Drawing Sheets

Specification includes a Sequence Listing.

```
-1000                                         ctggtctttg gatcactgtg
-0980 caactctgct tctagaacac tgagcacttt ttctggtcta ggaattatga
-0930 ctttgagaat ggagtccgtc cttccaatga ctccctcccc attttcctat
-0880 ctgcctacag gcagaattct cccccgtccg tattaaataa acctcatctt
-0830 ttcagagtct gctcttatac caggcaatgt acacgtctga gaaacccttg
-0780 ccccagacag ccgttttaca cgcaggaggg gaaggggagg ggaaggagag
-0730 agcagtccga ctctccaaaa ggaatccttt gaactagggt ttctgactta
-0680 gtgaacccccg cgctcctgaa aatcaaggt tgaggggta gggggacact
-0630 ttctagtcgt acaggtgatt tcgattctcg gtggggctct cacaactagg
-0580 aaagaatagt tttgctttt cttatgatta aaagaagaag ccatactttc
-0530 cctatgacac caaacacccc gattcaattt ggcagttagg aaggttgtat
-0480 cgcggaggaa ggaaacgggg cggggcgga tttctttta acagagtgaa
-0430 cgcactcaaa cacgcctttg ctggcaggcg gggagcgcg gctgggagca
-0380 gggaggccgg agggcggtgt ggggggcagg tggggaggag cccagtcctc
-0330 cttccttgcc aacgctggct ctggcgaggg ctgcttccgg ctggtgcccc
-0280 cgggggagac ccaacctggg gcgacttcag gggtgccaca ttcgctaagt
-0230 gctcggagtt aatagcacct cctccgagca ctcgctcacg gcgtcccctt
-0180 gcctggaaag ataccgcggt ccctccagag gatttgaggg acaggtcgg
-0130 aggggctct tccgccagca ccggaggaag aaagaggagg ggctggctgg
-0080 tcaccagagg gtggggcgga ccgcgtgcgc tcggcggctg cggagagggg
-0030 gagagcaggc agcgggcggc ggggagcagc ATG
```

FIG. 1

```
-2800                                         ccatttttatt tatttattta
-2780 ttttattttt tagctgtaag cccaaggcag cagtttgcgg tatttatata
-2730 atgacatata gaagtaggta gaggatgtca gacaccctgc aaacatccaa
-2680 gtaggataca tctaacaacc aactccctag ccaaatctga catagatgcc
-2630 ctatgaaaat tagtgtaaag tcactgcttt tatagctaca tctgcataga
-2580 tcccctgtat gaaagcatgt actacctgga taataatatc tgtattttttc
-2530 tgtagtagga aatcagtgta gttttaaaa ccaaaaagta ttgttattaa
-2480 tctatctttg atctcaaaca atttcaatga cctagtatag tgatttctac
-2430 ggaaagccct gcaatttact caaagcagtt tttaaatatt gttttaaaag
-2380 tgtgtgtgtg tgtgtgtgtg tgtgtgtgtg tgtgtgtggt gttaaagtca
-2330 ttttcaaacc cctcacaatg tcttgaatgt gacatttgag tcatttatgg
-2280 taacttataa ctcctttgaa gaagttattc agaattgagg ttccagacac
-2230 acaaatgcac aatacaccat ttttccttcc agttaacaat cagagggcaa
-2180 cacttatttt taaaggaaaa tcgactccat aagggacttt ataaaggggt
-2130 agacataaac cagtatcagg gataaactct ccgttcccct gtttaaccta
-2080 attttcccag ggccatcctg gaatacgaat tttctcttga aatacagtca
-2030 aagaaaaagt ggtaggctac agagcagagg aaacactgga cacagcgacc
-1980 caccccagag tcacttccct taatctaatg actaggtttt ttctgaaagt
-1930 tattttgtta gaacacagga acttttgcga ccacagtgat gcttttagag
-1880 ggttgaatcc tcaaaagaa aattaatcgc aactagtaga agggagatta
-1830 cttattgatt cttataactt ctgcaggaat acacagttat gagttagggc
-1780 aaagagaaaa ttgacttta atattctcta tcactaacat gagagaacat
-1730 gtatgtgttc caaaataatt tttatttatt gaaacccgc tatatacctg
-1680 gattttcaca gaatattcat tactctccaa aatggccttt tctaggtgaa
-1630 ttttatttc cttacagacc tcaagaagtt tacataattt acttaaacct
-1580 gaggagagag aacaaagcct cagaaaattt acatagttta tttaaactaa
-1530 actcagcttg cttggtagca gcttctaatc ccagcagtta aagagacaga
-1480 agcagggcca acctggggta taatataagg tgagactctc ctttctttct
-1430 ctctgtctct gtctgtctct gtctctgtgt gtgtgtgtgt gtgtgtgtgt
-1380 gtgtgtgtgt gtctcctctc tctctctctc tctctctctc tctctctctc
-1330 tgtctctctc tccctccccc tccctccctc tcccctcct ctctccctcc
-1280 ctctccctcc ccccccccca cacatttgaa ttcgtggagt tggtaaatga
-1230 ggggtcagtt ctctgtctgt ctgtagtttt gtgtccacag gatatgactg
-1180 acattctcac cacacacata caaagtcaaa aatagctgtg gccatataaa
-1130 gaatatgggg agagaaaatt attcaaaatc tgcagaaaat aatgccaggc
```

FIG. 2A

```
-1080 ctttaatcct ggcacccagg aggcagaagg gagacagagt tctgagttta
-1030 tgctgagttc caggagtgga agaaagggcc attgcctttc tggtgaggac
-0980 tgtcttttta aatcctccct tctgtccagt actggtaact ctgcccaaag
-0930 cgtgttcttc ttcctgcctc acaagattgc aaagacgttt ttaacgaaca
-0880 atttaaaccg gtgcaacgtt tatgcgcagc acaccaactc atttaaacaa
-0830 acaacagccc cataaaatag aaatacttta taagcagatt gccctccgat
-0780 gacttcaccc cgtcactttt ttatagttgt gtacagaatc ctagcactga
-0730 tacagcaaca tcagaaatgt ttctgcaaat ccttcgcaaa gattcggatt
-0680 tcatactggg cgtggtaccc tccaaaatga gttgtttgag ctagggttgt
-0630 tgggatctca gcttggcgaa gttgtagctc tttcttctga ataaaagatg
-0580 acacaatttt ctgctaagat gttaaatacc ttaagtttca gtgtagtgat
-0530 gaaaattacc ctccttcgtt tttctaatac ctgggtgttg cactggggag
-0480 gaaggagaga tttcgagaag gactagttca ctttctcaga agacacgtgt
-0430 gcacttcttt gctgtgcggg tccagaagga gcccagcgtg tcaaagggtg
-0380 accaggcatg ggggaggggt gttagcgtgg gtagcaggcg ggggctgtcc
-0330 gatcctttag cgctgtttca acgccagct ctcctcctga acctgcatc
-0280 tcttctgtag tccgggctcc atccctttcc cctcccccat ccggaggtgg
-0230 ggggaacagc agtgttttca ggggtgttca attcatgcta tattcagggc
-0180 aaatagcgcc acctatggcg ggctgtggag ccaggtcagg agcagagtgt
-0130 ggctccccc ccccccaca ccatcctcag aggaaggaag gagggaccca
-0080 ctggtcacac gactgggcga ttgggcgggc actgaatctc cgcgaggaaa
-0030 gcgaactcga ggagagccat ctggagcagc ATG
```

FIG. 2B

```
atggacttca gcagaaatct ttatgatatt ggggaacaac tggacagtga
agatctggcc tccctcaagt tcctgagcct ggactacatt ccgcaaagga
agcaagaacc catcaaggat gccttgatgt tattccagag actccaggaa
aagagaatgt tggaggaaag caatctgtcc ttcctgaagg agctgctctt
ccgaattaat agactggatt tgctgattac ctacctaaac actagaaagg
aggagatgga aagggaactt cagacaccag gcagggctca aatttctgcc
tacagggtca tgctctatca gatttcagaa gaagtgagca gatcagaatt
gaggtctttt aagtttcttt tgcaagagga aatctccaaa tgcaaactgg
atgatgacat gaacctgctg gatattttca tagagatgga gaagagggtc
atcctgggag aaggaaagtt ggacatcctg aaaagagtct gtgcccaaat
caacaagagc ctgctgaaga taatcaacga ctatgaagaa ttcagcaaag
gggaggagtt gtgtgggta atgacaatct cggactctcc aagagaacag
gatagtgaat cacagacttt ggacaaagtt taccaaatga aaagcaaacc
tcggggatac tgtctgatca tcaacaatca caattttgca aaagcacggg
agaaagtgcc caaacttcac agcattaggg acaggaatgg aacacacttg
gatgcagggg ctttgaccac gacctttgaa gagcttcatt ttgagatcaa
gccccacgat gactgcacag tagagcaaat ctatgagatt ttgaaaatct
accaactcat ggaccacagt aacatggact gcttcatctg ctgtatcctc
tcccatggag acaagggcat catctatggc actgatggac aggaggcccc
catctatgag ctgacatctc agttcactgg tttgaagtgc ccttcccttg
ctggaaaacc caaagtgttt tttattcagg cttgtcaggg gataactac
cagaaaggta tacctgttga gactgattca gaggagcaac cctatttaga
aatggattta tcatcacctc aaacgagata tatcccggat gaggctgact
ttctgctggg gatggccact gtgaataact gtgtttccta ccgaaaccct
gcagagggaa cctggtacat ccagtcactt tgccagagcc tgagagagcg
atgtcctcga ggcgatgata ttctcaccat cctgactgaa gtgaactatg
aagtaagcaa caaggatgac aagaaaaaca tggggaaaca gatgcctcag
cctactttca cactaagaaa aaaacttgtc ttcccttctg attga
```

FIG. 3

COMPOSITION COMPRISING A GENE VECTOR THAT SELECTIVELY DEPLETES P16 POSITIVE SENESCENT CELLS

CROSS-REFERENCE TO RELATED APPLICATION

This application is a continuation of U.S. patent application Ser. No. 16/029,244, filed Jul. 6, 2018, which is a divisional of U.S. patent application Ser. No. 14/394,854, filed Oct. 16, 2014, which is a U.S. 371 of International PCT/US2013/036811, filed Apr. 16, 2013, which claims the benefit and priority under 35 U.S.C. § 119 (e) to U.S. Provisional Application No. 61/625,612, filed Apr. 17, 2012, the content of which is incorporated by reference in its entirety into the present disclosure.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 44237-716-301-Sequence-Listing.txt. The text file is 8 KB, and was created on Jun. 7, 2019, and is being submitted electronically via EFS-Web.

BACKGROUND

Senescent cells accumulate in people as a result of stress, injuries, aging, and related insults leading to a multitude of diseases, conditions and pathologies. The removal of senescent cells could therefore provide a dramatic improvement in the quality of life of most humans.

Studies using genetically engineered mice have demonstrated that the destruction of senescent cells in a living organism reverses many disease-like pathologies. Unfortunately, unique exploitable markers (such as surface epitopes) that can be exploited to design drugs for the specific killing of senescent cells have not yet been identified. Thus, there is a need in the art for methods and compositions designed to specifically target and eliminate these cells in vivo. Ideally, elimination of such cells should occur through natural mechanisms such as apoptosis.

SUMMARY

This invention provides for polynucleotides, viruses, methods and compositions which are useful for the activation of apoptosis of senescent cells. One aspect relates to a polynucleotide comprising a pro-apoptotic gene and a p16 promoter, wherein the expression of the pro-apoptotic gene is regulated by the p16 promoter or an equivalent thereof.

A second aspect relates to a virus comprising the polynucleotides as described herein. In one embodiment, the virus is a lytic virus.

Further aspects relate to pharmaceutical compositions comprising the polynucleotides or virus particles as described herein.

Another aspect relates to a method for expressing a pro-apoptotic gene in a senescent cell comprising administering to the cell the polynucleotide, virus, or pharmaceutical composition as described herein.

A further aspect relates to a method for inducing apoptosis in a senescent cell comprising administering to the cell the polynucleotide, virus, or pharmaceutical composition as described herein. In certain embodiments, the p16 promoter is activated in the cell. In further embodiments, the cell is in vivo in a mammal. In another embodiment, the cell is in vitro.

Another aspect relates to a A conditionally replicating viral construct comprising an essential viral gene regulated by one or more promoters wherein at least one promoter is the p16 promoter or an equivalent thereof. Also provided, is a method for expressing a conditionally replicating virus in a cell comprising infecting the cell with the virus as described herein, wherein the virus replicates in senescent cells but not in non-senescent cells.

A further method disclosed herein relates to a method for inducing apoptosis in a senescent cell in a subject in need thereof comprising administering to the subject a polynucleotide, virus, host cell, or pharmaceutical composition described herein.

Other aspects relate to pharmaceutical compositions comprising the polynucleotide or virus described herein and a carrier.

BRIEF DESCRIPTION OF THE FIGURES

FIG. 1 shows SEQ ID NO: 1, which comprises the human p16 promoter. This promoter sequence is further described in Wang et al. "Characterization of Regulatory Elements on the Promoter Region of p16INK4a That contribute to Overexpression of p16 in Senescent Fibroblasts" J. of Biol. Chem. (2001), Vol. 276, No. 52, pp. 48655-48661, which is herein incorporated by reference.

FIG. 2A-B shows SEQ ID NO: 2, which comprises the mouse p16 promoter.

FIG. 3 shows SEQ ID NO: 3, which exemplifies a Caspase 8 polynucleotide sequence from humans.

DETAILED DESCRIPTION OF THE INVENTION

Throughout this disclosure, various technical and patent publications are referenced to more fully describe the state of the art to which this invention pertains. These publications are incorporated by reference, in their entirety, into this application.

Definitions

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, $3^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, 3$^{rd}$ edition (Cold Spring Harbor Laboratory Press (2002)).

As used herein, certain terms may have the following defined meanings.

As used in the specification and claims, the singular form "a," "an" and "the" include plural references unless the context clearly dictates otherwise.

As used herein, the term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of" shall mean excluding more than trace elements of other ingredients and substantial method steps for preparing the microfluidic device. Embodiments defined by each of these transition terms are within the scope of this invention.

All numerical designations, e.g., pH, temperature, time, concentration, and molecular weight, including ranges, are approximations which are varied (+) or (-) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

The term "construct" or "DNA construct" refers to an engineered fragment of DNA containing genes and other functional elements. The construct may be linear or circular. Examples of DNA constructs include plasmids, cosmids, expression vectors, phagemids, fosmids, and artificial chromosomes such as bacterial artificial chromosomes, yeast artificial chromosomes, and human artificial chromosomes.

The term "protein", "peptide" and "polypeptide" are used interchangeably and in their broadest sense refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "isolated" or "recombinant" as used herein with respect to nucleic acids, such as DNA or RNA, refers to molecules separated from other DNAs or RNAs, respectively that are present in the natural source of the macromolecule as well as polypeptides. The term "isolated or recombinant nucleic acid" is meant to include nucleic acid fragments which are not naturally occurring as fragments and would not be found in the natural state. The term "isolated" is also used herein to refer to polynucleotides, polypeptides and proteins that are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart. In certain embodiments, the polypeptides and/or polynucleotides described herein are isolated and/or recombinant polypeptides or polynucleotides.

The term "pro-apoptotic gene" refers to a gene that promotes apoptosis in a cell. Apoptosis is the process of programmed cell death that may occur in multicellular organisms. Biochemical events lead to characteristic cell changes (morphology) and cell death. These changes include blebbing, cell shrinkage, nuclear fragmentation, chromatin condensation, and chromosomal DNA fragmentation. Non-limiting examples of pro-apoptotic genes include caspases, Bik, Puma, Bim, Bax, Bak, Bid, Bad, Bmf, Noxa, and Hrk.

The term "caspase" refers to proteases that play essential roles in apoptosis (programmed cell death) and necrosis. At least 12 caspases have been identified in humans. There are two types of apoptotic caspases: initiator (apical) caspases and effector (executioner) caspases. Initiator caspases (e.g., CASP2 (Genbank Accession: NM_001224.4), CASP8 (Genbank Accession: NM_001080124.1), CASP9 (Genbank Accession: NM_001229.3), and CASP10 (Genbank Accession: NM_001206524.1)) cleave inactive pro-forms of effector caspases, thereby activating them. Effector caspases (e.g., CASP3 (Genbank Accession: NM_004346.3), CASP6 (Genbank Accession: NM_001226.3), CASP7 (Genbank Accession: NM_001227.3)) in turn cleave other protein substrates within the cell, to trigger the apoptotic process. The initiation of this cascade reaction is regulated by caspase inhibitors.

The term "p16" refers to Cyclin-dependent kinase inhibitor 2A, (CDKN2A, p16$^{Ink4A}$) also known as multiple tumor suppressor 1 (MTS-1). It has roles in tumor suppression and is expressed in senescent cells. The p16 gene is regulated by a promoter that is activated in senescent cells. A promoter is a region of DNA that facilitates or regulates the transcription of a particular gene. Promoters are located near the genes they regulate, on the same strand and typically upstream (towards the 5' region of the sense strand).

The term "senescent cell" refers to a cell that has lost the ability to divide. A cell may stop dividing due to a variety of factors such as, for example, cellular damage, DNA damage, and/or toxins. A senescent cell may be a cultured cell or a cell in the body, in vivo.

It is to be inferred without explicit recitation and unless otherwise intended, that when the present invention relates to a polypeptide, protein, polynucleotide or antibody, an equivalent or a biologically equivalent of such is intended within the scope of this invention. As used herein, the term "biological equivalent thereof" is intended to be synonymous with "equivalent thereof" when referring to a reference protein, antibody, polypeptide or nucleic acid, intends those having minimal homology while still maintaining desired structure or functionality. Unless specifically recited herein, it is contemplated that any polynucleotide, polypeptide or protein mentioned herein also includes equivalents thereof. For example, an equivalent intends at least about 70% homology or identity, or alternatively about 80% homology or identity and alternatively, at least about 85%, or alternatively at least about 90%, or alternatively at least about 95% or alternatively 98% percent homology or identity and exhibits substantially equivalent biological activity to the reference protein, polypeptide or nucleic acid. In another aspect, the term intends a polynucleotide that hybridizes under conditions of high stringency to the reference polynucleotide or its complement.

A polynucleotide or polynucleotide region (or a polypeptide or polypeptide region) having a certain percentage (for example, 80%, 85%, 90% or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 30% identity or alternatively less than 25% identity, less than 20% identity, or alternatively less than 10% identity with one of the sequences of the present invention.

"Homology" or "identity" or "similarity" can also refer to two nucleic acid molecules that hybridize under stringent conditions to the reference polynucleotide or its complement.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1× SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

The term "essential viral gene" refers to a viral gene required for an essential function of the virus. The function may be integration, replication, or viral structure. Exemplary essential viral genes include gag, pol, and env. Gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome.

The term "chemically inducible promoter" refers to a promoter whose activity is induced by the presence or absence of a chemical. One example of a chemically inducible promoters is the alcohol dehydrogenase I promoter, which can be induced by different agricultural alcohol-based formulations. The tetracycline-regulated promoter systems also provide an example of a chemically inducible promoter. The tetracycline promoters can function either to activate or repress gene expression in the presence of tetracycline. Some of the elements of the systems include a tetracycline repressor protein (TetR), a tetracycline operator sequence (tetO) and a tetracycline transactivator fusion protein (tTA), which is the fusion of TetR and a herpes simplex virus protein 16 (VP16) activation sequence. Also included within this disclosure are steroid regulated promoters such as promoters based on the rat glucocorticoid receptor, promoters based on the human estrogen receptor, and promoters based on ecdysone receptors derived from different moth species. Other chemically inducible promoters are known in the art. It is within the knowledge of the skilled artisan to select a chemically inducible promoter based on factors such as cell type, deliver system, etc. . . .

A "gene" refers to a polynucleotide containing at least one open reading frame (ORF) that is capable of encoding a particular polypeptide or protein after being transcribed and translated. Any of the polynucleotide or polypeptide sequences described herein may be used to identify larger fragments or full-length coding sequences of the gene with which they are associated. Methods of isolating larger fragment sequences are known to those of skill in the art.

The term "express" refers to the production of a gene product.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

A "gene product" or alternatively a "gene expression product" refers to the amino acid (e.g., peptide or polypeptide) generated when a gene is transcribed and translated.

"Under transcriptional control" or "regulated by" is a term well understood in the art and indicates that transcription of a polynucleotide sequence, usually a DNA sequence, depends on its being operatively linked to an element which contributes to the initiation of, or promotes, transcription.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

"Pharmaceutically acceptable carriers" or "carriers" refers to any diluents, excipients or carriers that may be used in the compositions of the invention. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They are preferably selected with respect to the intended form of administration, that is, oral tablets, capsules, elixirs, syrups and the like and consistent with conventional pharmaceutical practices.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated and target cell or tissue. Non-limiting examples of route of administration include oral administration, nasal administration, injection and topical application.

In the case of an in vitro application, in some embodiments the effective amount will depend on the size and nature of the application in question. It will also depend on the nature and sensitivity of the in vitro target and the methods in use. The skilled artisan will be able to determine the effective amount based on these and other considerations. The effective amount may comprise one or more administrations of a composition depending on the embodiment.

The agents and compositions can be used in the manufacture of medicaments and for the treatment of humans and other animals by administration in accordance with conventional procedures, such as an active ingredient in pharmaceutical compositions.

An agent of the present invention can be administered for therapy by any suitable route of administration. It will also be appreciated that the preferred route will vary with the condition and age of the recipient and the disease being treated.

A "viral vector" is defined as a recombinantly produced virus or viral particle that comprises a polynucleotide to be delivered into a host cell, either in vivo, ex vivo or in vitro. Examples of viral vectors include retroviral vectors, lentiviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Curr. Opin. Biotechnol. 5:434-439 and Ying, et al. (1999) Nat. Med. 5(7):823-827.

In aspects where gene transfer is mediated by a lentiviral vector, a vector construct or backbone refers to the polynucleotide comprising the lentiviral genome or part thereof, and a therapeutic gene. As used herein, "lentiviral mediated gene transfer" or "lentiviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. Retroviruses carry their genetic information in the form of RNA; however, once the virus infects a cell, the RNA is reverse-transcribed into the DNA form which integrates into the genomic DNA of the infected cell. The integrated DNA form is called a provirus. As used herein, lentiviral vector refers to a viral particle capable of introducing exogenous nucleic acid into a cell through a viral or viral-like entry mechanism. A "lentiviral vector" is a type of retroviral vector well-known in the art that has certain advantages in transducing nondividing cells as compared to other retroviral vectors. See, Trono D. (2002) Lentiviral vectors, New York: Spring-Verlag Berlin Heidelberg.

Lentiviral vectors of this invention may be based on or derived from oncoretroviruses (the sub-group of retroviruses containing MLV), and lentiviruses (the sub-group of retroviruses containing HIV). Examples include ASLV, SNV and RSV all of which have been split into packaging and vector components for lentiviral vector particle production systems. The lentiviral vector particle according to the invention may be based on a genetically or otherwise (e.g. by specific choice of packaging cell system) altered version of a particular retrovirus.

That the vector particle according to the invention is "based on" or has a "backbone" of a particular retrovirus means that the vector is derived from that particular retrovirus. The genome of the vector particle comprises components from that retrovirus as a backbone. The vector particle contains essential vector components compatible with the RNA genome, including reverse transcription and integration systems. Usually these will include gag and pol proteins derived from the particular retrovirus. Thus, the majority of the structural components of the vector particle will normally be derived from that retrovirus, although they may have been altered genetically or otherwise so as to provide desired useful properties. However, certain structural components and in particular the env proteins, may originate from a different virus. The vector host range and cell types infected or transduced can be altered by using different env genes in the vector particle production system to give the vector particle a different specificity.

A "subject," "individual" or "patient" is used interchangeably herein, and refers to a vertebrate, preferably a mammal, more preferably a human. Mammals include, but are not limited to, murines, rats, rabbit, simians, bovines, ovine, porcine, canines, feline, farm animals, sport animals, pets, equine, and primate, particularly human. Besides being useful for human treatment, the present invention is also useful for veterinary treatment of common laboratory mammals, including rodents, rabbits, mice, and the like.

"Host cell" refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present invention for any particular subject depends upon a variety of factors including the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for patient administration. In general, one will desire to administer an amount of the compound that is effective to achieve a serum level commensurate with the concentrations found to be effective in vitro. Determination of these parameters is well within the skill of the art. These considerations, as well as effective formulations and administration procedures are well known in the art and are described in standard textbooks.

The term administration shall include without limitation, administration by oral, parenteral (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration. The invention is not limited by the route of administration, the formulation or dosing schedule. Administration may also refer to the transfer of genetic material (i.e. polynucleotides) to the human body. Methods of gene transfer are known in the art and are described herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above.

DESCRIPTIVE EMBODIMENTS

Senescent cells, but not non-senescent cells, express the p16 gene (a cell cycle dependent kinase inhibitor). The expression of the p16 gene is the result of p16 promoter activation in senescent cells. Described herein are methods and compositions that can be used to increase the expression of caspases through p16 promoter activation in senescent cells.

Polynucleotides

One aspect relates to a polynucleotide comprising a pro-apoptotic gene and a p16 promoter, wherein the expression of the pro-apoptotic gene is regulated by the p16 promoter or an equivalent thereof. The p16 promoter can be a canonical p16 promoter (See, for e.g. Nature. 2011 Nov. 10; 479(7372):232-6 which is incorporated by reference for all purposes) or a non-cononical p16 promoter. The promoter sequence is also disclosed in the gene sequence for the p16 gene (Genbank Accession Nos: NC_000009.11, GI:224589821, and AF527803.1 which are herein incorporated by reference for all purposes). The promoter sequence is the sequence upstream (towards the 5' region of the sense strand) of the transcription start site of the gene. The promoter sequence of p16 as well as discreet binding elements in the p16 promoter are disclosed in the art, and a skilled artisan would be able to identify an appropriate portion of or all of the p16 promoter to use when practicing the invention. Additional elements may be inserted into the promoter or as sequences upstream or downstream of the promoter or coding sequences present on the DNA construct. Such elements include enhancers (such as, for example, SV40 and the Ig enhancer), and transcription binding elements. Other enhancer/silencer/insulator sequences are further described in U.S. Pat. Pub. Nos.: 2010/0158879, 2007/0172949, 2003/0229046, 2002/0133838, 2002/0066117 and 20040076954, each of which are herein incorporated by reference in their entirety. It is contemplated that the addition of these additional elements will fine-tune the activity of the p16 promoter to make the promoter stronger, weaker, temporally-regulated, spatially-regulated, tissue-specific, and/or inducible by physical and chemical inducers, for example.

The p16 promoter may be from any species. In certain embodiments, the p16 promoter is from a mammal. In further embodiments, the p16 promoter comprises the human, mouse, or rat p16 promoter, an equivalent thereof, a fragment thereof, or a polynucleotide having at least 80% identity to the human or mouse p16 promoter. In further embodiments, the p16 promoter comprises a polynucleotide having at least 70%, 75%, 80%, 85%, 90%, 95%, or 99% identity to the human, mouse, or rat promoter.

In one embodiment, the human p16 promoter comprises SEQ ID NO: 1 or a fragment or equivalent thereof. This sequence exemplifies 1000 bp upstream of start codon (ATG). Regulatory elements that contribute to overexpression of p16 in senescent cells are in the region of −622 to −280 bp. A negative regulatory element, the INK4a transcription silence element (ITSE) is at −491 to −485 bp of SEQ ID NO: 1. The GC-rich region of the p16 promoter from −466 to −451 of SEQ ID NO: 1 is a positive transcription regulatory element. Deletion of this region showed 91.4% loss of p16 promoter activity in senescent cells (Wang et al. "Characterization of Regulatory Elements on the Promoter Region of p16INK4a That contribute to Overexpression of p16 in Senescent Fibroblasts" J. of Biol. Chem. (2001), Vol. 276, No. 52, pp. 48655-48661). Regulatory elements believed to be important within the p16 promoter region include Region A (−507 to −493 bp of SEQ ID NO: 1), Region B (−491 to −485 bp of SEQ ID NO: 1), and Region C (−466 to −450 bp of SEQ ID NO: 1). In certain embodiments, the human p16 promoter retains at least 80%, 90%, 95%, or 95% to one or more of Regions A, B, or C.

In a further embodiment, the mouse p16 promoter comprises SEQ ID NO: 2. This sequence exemplifies 2800 bp upstream of start codon (ATG).

The pro-apotic gene may be a pro-apoptotic gene from any species. Preferably, the pro-apotic gene corresponds to a mammalian pro-apotic gene. Non-limiting examples of pro-apoptotic genes include caspase, Bik, Puma, Bim, Bax, Bak, Bid, Bad, Bmf, Noxa, and Hrk. In one embodiment, the pro-apoptotic gene is a caspase. In certain embodiments, the caspase is a human caspase. Expression of the caspase in a senescent cell may induce apoptosis of the senescent cell, thereby eliminating the senescent cell and reducing the risk of disease. Accordingly, in certain embodiments, the caspase is one that is involved in the apoptosis pathway of the cell. In a specific embodiment the caspase is caspase 8 (See, for e.g., *Nature Medicine* 11, 797-803 (2005) which is incorporated by reference for all purposes). In another embodiment, the caspase is a chemically dimerizable cyclophilin binding protein caspase (See, for e.g., *Nature Medicine* 11, 797-803 (2005), which is herein incorporated by reference in its entirety). In a further embodiment, the caspase comprises the nucleotide sequence of SEQ ID NO: 3, an equivalent thereof, a fragment thereof, or a polynucleotide having at least 70%, 75%, 80%, 85%, 90%, 95%, or 99% sequence identity to SEQ ID NO: 3.

The polynucleotide may include further elements that render the polynucleotide suitable for expression in a host cell or host senescent cell. Such elements include antibiotic resistance genes, origins of replication, and termination sequences, for example. The polynucleotide may further comprise markers that enable the tracking and expression of the polynucleotice in cells. Such markers may include fluorescent labels and the like. The markers and elements of the polynucleotide may be under the expression of one promoter or multiple promoters.

Viruses

Described herein is the production of viruses engineered to induce apoptosis in cells that are expressing or containing factors that activate the p16 promoter. Activation of the p16 promoter is prevalent in senescent cells but not in non-senescent cells. Thus, it is contemplated that infecting a cell with virus comprising an apoptosis inducing factor such as a pro-apoptotic gene (i.e. caspase) regulated by the p16 promoter will induce apoptosis in cells expressing and/or containing factors capable of activating the p16 promoter. The promoter may be the standard p16 promoter or an equivalent or comprise SEQ ID NO: 1 or 2. The promoter may also contain additional elements that enhance or reduce the expression of downstream genes.

This disclosure features methods and compositions for expressing a gene in a cell. In one aspect, the disclosure features methods of gene therapy to express a gene or protein in a cell, such as a senescent cell of a patient. Gene therapy, including the use of viral vectors as described herein, seeks to transfer new genetic material (e.g., polynucleotides encoding pro-apoptotic genes or other proteins or a biologically active fragment thereof) to the cells of a patient with resulting therapeutic benefit to the patient.

For in vivo gene therapy, expression vectors encoding the gene of interest is administered directly to the patient. The vectors are taken up by the target cells (e.g., senescent cells) and the gene expressed. Recent reviews discussing methods and compositions for use in gene therapy include Eck et al., in Goodman & Gilman's The Pharmacological Basis of Therapeutics, Ninth Edition, Hardman et al., eds., McGray-Hill, New York, 1996, Chapter 5, pp. 77-101; Wilson (1997) Clin. Exp. Immunol. 107 (Suppl. 1):31-32; Wivel et al. (1998) Hematology/Oncology Clinics of North America, Gene Therapy, S. L. Eck, ed., 12(3):483-501; Romano et al. (2000) Stem Cells 18:19-39, and the references cited therein. U.S. Pat. No. 6,080,728 also provides a discussion of a wide variety of gene delivery methods and compositions.

In one embodiment, the virus is capable of infecting non-dividing cells (i.e. a lentivirus). In one aspect, the backbone contains essential sequences for integration into a target cell genome.

In one aspect, the term "virus" intends a recombinant viral vector that retains the ability to infect and transduce non-dividing and/or slowly-dividing cells and integrate into the target cell's genome. In several aspects, the vector is derived from or based on a wild-type virus. In further aspects, the vector is derived from or based on a wild-type lentivirus. Examples of such, include without limitation, human immunodeficiency virus (HIV), equine infectious anaemia virus (EIAV), simian immunodeficiency virus (SIV) and feline immunodeficiency virus (FIV). Alternatively, it is contemplated that other retrovirus can be used as a basis for a vector backbone such murine leukemia virus (MLV). It will be evident that a viral vector according to the invention need not be confined to the components of a particular virus. The viral vector may comprise components derived from two or more different viruses, and may also comprise synthetic components. Vector components can be manipulated to obtain desired characteristics, such as target cell specificity.

Adenoviruses are able to transfect a wide variety of cell types, including non-dividing cells. There are more than 50 serotypes of adenoviruses that are known in the art, but the most commonly used serotypes for gene therapy are type 2 and type 5. These viruses may be rendered replication-defective and genetically-modified to prevent unintended spread of the virus. This is normally achieved through the deletion of the E1 region, deletion of the E1 region along with deletion of either the E2 or E4 region, or deletion of the entire adenovirus genome except the cis-acting inverted terminal repeats and a packaging signal (Gardlik et al. (2005) Med. Sci. Monit. 11: RA110-121). In certain embodiments, the virus is not replication defective.

Retroviruses are also useful as gene therapy vectors and usually (with the exception of lentiviruses) are not capable of transfecting non-dividing cells. Accordingly, any appropriate type of retrovirus that is known in the art may be used, including, but not limited to, HIV, SIV, FIV, EIAV, and Moloney Murine Leukaemia Virus (MoMLV).

In another aspect, the invention features the methods of gene therapy that utilize a lentiviral vector to express pro-apoptotic genes, or other proteins in a patient. Lentiviruses are a type of retroviruses with the ability to infect both proliferating and quiescent cells. An exemplary lentiviral vector for use in gene therapy is the HIV-1 lentivirus. Previously constructed genetic modifications of lentiviruses include the deletion of all protein encoding genes except those of the gag, pol, and rev genes (Moreau-Gaudry et al. (2001) Blood 98:2664-2672).

Adeno-associated virus (AAV) vectors can achieve latent infection of a broad range of cell types, exhibiting the desired characteristic of persistent expression of a therapeutic gene in a patient. The invention includes the use of any appropriate type of adeno-associated virus known in the art including, but not limited to AAV1, AAV2, AAV3, AAV4, AAV5, and AAV6 (Lee et al. (2005) Biochem. J. 387: 1-15; U.S. Patent Publication 2006/0204519).

Herpes simplex virus (HSV) replicates in epithelial cells, but is able to stay in a latent state in non-dividing cells such as the midbrain dopaminergic neurons. The gene of interest may be inserted into the LAT region of HSV, which is expressed during latency. Other viruses that have been shown to be useful in gene therapy include parainfluenza viruses, poxviruses, and alphaviruses, including Semliki forest virus, Sinbis virus, and Venezuelan equine encephalitis virus (Kennedy (1997) Brain 120: 1245-1259).

With regard to the structural genes gag, pol and env themselves, gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome.

For the production of viral vector particles, the vector RNA genome is expressed from a DNA construct encoding it in a host cell. The components of the particles not encoded by the vector genome are provided in trans by additional nucleic acid sequences (the "packaging system", which usually includes either or both of the gag/pol and env genes) expressed in the host cell. The set of sequences required for the production of the viral vector particles may be introduced into the host cell by transient transfection, or they may be integrated into the host cell genome, or they may be provided in a mixture of ways. The techniques involved are known to those skilled in the art.

Retroviral vectors for use in this invention include, but are not limited to Invitrogen's pLenti series versions 4, 6, and 6.2 "ViraPower" system. Manufactured by Lentigen Corp.; pHIV-7-GFP, lab generated and used by the City of Hope Research Institute; "Lenti-X" lentiviral vector, pLVX, manufactured by Clontech; pLKO.1-puro, manufactured by Sigma-Aldrich; pLemiR, manufactured by Open Biosystems; and pLV, lab generated and used by Charité Medical School, Institute of Virology (CBF), Berlin, Germany.

Also provided are conditionally replicating viruses in which regulatory elements responsible for the expression of essential viral genes are replaced by the p16 promoter as described herein to ensure that the viruses will replicate and subsequently kill only senescent cells.

Suitable viruses may include, by way of non-limiting examples, Adeno-associated virus, Australian bat lyssavirus, BK polyomavirus, Banna virus, Barmah forest virus, Bunyamwera virus, Bunyavirus La Crosse, Bunyavirus snowshoe hare, Cercopithecine herpesvirus, Cercopithecine herpesvirus, Chandipura virus, Chikungunya virus, Cowpox virus, Coxsackievirus, Crimean-Congo hemorrhagic fever virus, Dengue virus, Dhori virus, Dugbe virus, Duvenhage virus, Eastern equine encephalitis virus, Ebolavirus, Echovirus, Encephalomyocarditis virus, Epstein-Barr virus, European bat lyssavirus, GB virus C, Hantaan virus, Hendra virus, Hepatitis A virus, Hepatitis B virus, Hepatitis C virus, Hepatitis E virus, Hepatitis delta virus, Human herpesvirus 1, Horsepox virus, Human adenovirus, Human astrovirus, Human coronavirus, Human cytomegalovirus, Human enterovirus 68, 70, Human herpesvirus 2, Human herpesvirus 6, Human herpesvirus 7, Human herpesvirus 8, Human immunodeficiency virus, Human papillomavirus, Human parainfluenza, Human parvovirus B19, Human respiratory syncytial virus, Human respiratory syncytial virus, Human respiratory syncytial virus, Human SARS coronavirus, Human spumaretrovirus, Human T-lymphotropic virus, Human torovirus, Influenza A virus, Influenza B virus, Influenza C virus, Isfahan virus, JC polyomavirus, Japanese encephalitis virus, Junin arenavirus, KI Polyomavirus, Kunjin virus, Lagos bat virus, Lake Victoria marburgvirus, Langat virus, Lassa virus, Lordsdale virus, Louping ill virus, Lymphocytic choriomeningitis virus, Machupo virus, Mayaro virus, Measles virus, Mengo encephalomyocarditis virus, Merkel cell polyomavirus, Mokola virus, Molluscum contagiosum virus, Monkeypox virus, Mumps virus, Murray valley encephalitis virus, New York virus, Nipah virus, Norwalk virus, O'nyong-nyong virus, Orf virus, Oropouche virus, Pichinde virus, Poliovirus, Punta toro phlebovirus, Puumala virus, Rabies virus, Rift valley fever virus, Ross river virus, Rotavirus A, Rotavirus B, Rotavirus C, Rubella virus, Sagiyama virus, Sandfly fever sicilian virus, Sapporo virus, Semliki forest virus, Seoul virus, Simian foamy virus, Simian virus 5, Sindbis virus, Southampton virus, St. louis encephalitis virus, Tick-borne powassan virus, Torque teno virus, Toscana virus, Uukuniemi virus, Vaccinia virus, Varicella-zoster virus, Variola virus, Venezuelan equine encephalitis virus, Vesicular stomatitis virus, Western equine encephalitis virus, WU polyomavirus, West Nile virus, Yaba monkey tumor virus, Yaba-like disease virus, Yellow fever virus.

While the list of virus above provides names of individual virus types, it is contemplated that any serotype from a given virus would be suitable for use. For instance there are more than 100 types of papillomaviruses and a dozen or more serotypes of adenovirus. Also useful are viruses not known to infect human cells but engineered in such fashion that they gain the ability to infect and or replicate lytically in human cells.

Viruses can be expressed in cells by methods common in the art. Methods of introduction of a virus in the cell include common methods of infection or transfection methods. When the methods are practiced in humans, it is preferred that the virus is introduced into the cell by infection.

Gene Transfer of Polypeptides

Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA. In vivo DNA-mediated gene transfer into a variety of different target sites has been studied extensively. Naked DNA may be administered using an injection, a gene gun, or electroporation. Naked DNA can provide long-term expression in muscle. See Wolff et al. (1992) Human Mol. Genet. 1:363-369; Wolff et al. (1990) Science 247: 465-1468. DNA-mediated gene transfer has also been characterized in liver, heart, lung, brain and endothelial cells. See Zhu et al. (1993) Science 261:209-211; Nabel et al. (1989) Science 244:1342-1344. DNA for gene transfer also may be used in association with various cationic lipids, polycations and other conjugating substances. See Przybylska et al. (2004) J. Gene Med. 6:85-92; Svahn et al. (2004) J. Gene Med. 6:S36-S44.

Methods of gene therapy using cationic liposomes are also well known in the art. Exemplary cationic liposomes for use in this invention are DOTMA, DOPE, DOSPA, DOTAP, DC-Chol, Lipid GL-67.TM., and EDMPC. These liposomes may be used in vivo or ex vivo to encapsulate a vector for delivery into target cells (e.g., neurons or pluripotent stem cells).

Pseudotyped Viral Particles

This invention further provides a method for producing a pseudotyped viral particle, comprising transducing a packaging cell line with the viral vector as described above, under conditions suitable to package the viral vector. Such conditions are known in the art and briefly described herein. The pseudotyped viral particle can be isolated from the cell supernatant, using methods known to those of skill in the art, e.g., centrifugation. Such isolated particles are further provided by this invention.

This invention further provides the isolated pseudotyped viral particle produced by this method. The pseudotyped viral particle comprises a polypeptide comprising a proapoptotic gene and a p16 promoter, wherein the expression of the pro-apoptotic gene is regulated by the p16 promoter or an equivalent thereof or embodiments of this polypeptide as described herein.

Yet further provided is an isolated cell or population of cells, comprising a polypeptide, viral particle, or viral vector as described herein. In one aspect, the isolated host cell is a packaging cell line.

Methods of the Invention

Aspects include methods for expressing a pro-apoptotic gene (i.e. caspase) in a senescent cell comprising administering to the cell a polynucleotide, viral particle, viral vector, or pharmaceutical composition as described herein. The expression of proteins in a cell can be determined by standard techniques known in the art. By way of example, such methods include, Southern blot analysis, western blot analysis, reverse-transcriptase PCR, real-time PCR, and the like. The cell may be one in which the p16 promoter is activated. However, it is not necessary to infect only cells with an activated p16 promoter since it is believed that the viruses described herein will only be active and replicate in cells in which the p16 promoter is activated.

Another method aspect relates to a method for inducing apoptosis in a senescent cell comprising administering to the cell a polynucleotide, viral particle, viral vector, or pharmaceutical composition as described herein. The cell may be a cell in cell culture or a cell in vivo, in the mammalian body.

Various assays can be used to determine the effectiveness of such methods. Assays that determine the level of cell death can be used and include, for example a TUNEL (Terminal deoxynucleotidyl transferase dUTP nick end labeling) assay. A TUNEL assay is a method for detecting DNA fragmentation by labeling the terminal end of nucleic acids. Another method of determining the level of cell death in cells is through propidium iodide labeling of cells. Propidium iodide is a DNA stain that can differentiate necrotic, apoptotic and normal cells. Live cells and dead cells can also be differentiated using trypan blue, a stain that colors dead tissues or dead cells blue. Other viability assays include but are not limited to ATP test, clonogenic assay, evans blue, flow cytometry, formazan-based assays, lactate dehydrogenase, methyl violet, and resazurin.

Pharmaceutical Compositions

The polypeptides, viral particles, and viral vectors as described herein may be combined with a carrier or a pharmaceutically acceptable carrier suitable for use of the compositions in the methods disclosed herein.

Compositions of the invention may be conventionally administered parenterally, by injection, for example, intravenously, subcutaneously, or intramuscularly. Additional formulations which are suitable for other modes of administration include oral formulations. Oral formulations include such normally employed excipients such as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%. In certain embodiments, a composition may be inhaled (e.g., U.S. Pat. No. 6,651,655, which is specifically incorporated by reference in its entirety). In the case of viral particles, the term administration includes the infection of a cell with the viral particle. Polypeptides and viral vectors of the disclosure may also be administered by various methods of gene transfer as described herein.

Typically, compositions of the invention are administered in a manner compatible with the dosage formulation, and in such amount as will be therapeutically effective. The quantity to be administered depends on the subject to be treated. Precise amounts of active ingredient required to be administered depend on the judgment of the practitioner.

The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in therapeutic compositions is contemplated.

The carrier may be a solvent or dispersion medium containing, for example, water, ethanol, polyol (for example, glycerol, propylene glycol, and liquid poly(ethylene glycol), and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

An effective amount of therapeutic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions will be administered in a manner compatible with the dosage formulation and in such amount as is therapeutically or prophylactically effective. The formulations are easily administered in a variety of dosage forms, such as the type of injectable solutions described above.

Treatment of Disease

It is contemplated that the methods described herein are useful in the treatment of diseases such as, for example, Diabetes, Heart Conditions, Obesity, Alzheimer's Disease, Dementia, Parkinson's Disease, Arthritis, Osteoarthritis, Osteoporosis, Loss of Vision, Loss of Hearing, Breathing problems, Coronary artery disease, Atherosclerosis, Melanocytic Nevi, Cancer, Asthma, Chronic Obstructive Pulmonary Disease, Fracture, Frailty, Hepatitis, Kidney Diseases, Muscle Fatigue, Skin conditions, and Hair loss.

EXAMPLES

Lentiviral production: To test whether senescent cells can be eliminated using a conditionally replicating virus, a canonical p16 promoter is cloned into a lentiviral vector. Caspase 8 is cloned downstream of the p16 promoter. Optionally, the promoters of essential lentiviral genes such as gag, pol and env are also replaced by the p16 promoter and/or a chemically inducible promoter. As a control, a lentiviral vector with a fluorescent marker instead of the caspase 8 gene is also constructed. The lentiviral constructs can then be transfected into a packaging cell line such as, for example, 293T cells. Transfection of the lentiviral constructs can be done using standard lipofectamine transfection techniques. If necessary, activation factors or chemical inducers are added to the cells to induce replication of the virus in the packaging cells. After culture of the cells for 24 hours or more, the virus-containing culture medium is removed from the cells and filter sterilized. The control (p16-fluorescent construct) and experimental (p16-caspase 8) virus are used in in vitro and in vivo experiments.

In vitro apoptosis of senescent cells: Mammalian cells are plated on a culture dish and passaged until replicative senescence is achieved in a majority of the cells. Senescence can be measured by, for example, a beta-galactosidase assay. Virus is added to the cell culture media of the senescent cells. The virus is removed after 24 hours, and fresh cell culture media is added to the cells. Optionally, more virus can be added after a 12-hour recovery. In parallel, control virus is added to a different dish of senescent cells. At 12, 24, 48, and 72 hours after removal of the virus, cells are harvested and real-time PCR is performed to test for the expression of caspase 8. In parallel, a TUNEL assay and caspase 8 immunofluorescence is performed to determine the level of apoptosis. The level of apoptosis with virus containing the p16-caspase 8 construct is compared to the level of apoptosis with the p16-fluorescent construct. It is contemplated that an increase in apoptosis will be observed in cells transfected with the caspase 8-containing construct.

In vivo apoptosis of senescent cells: Groups of mice can be inoculated with either control or experimental virus at the same titer in a volume of 100 µl. Animals of two groups can be inoculated subcutaneously in the scruff of the neck. Two, five, seven, fourteen, and 20 days after inoculation of the mice, individual mice can be sacrificed and tested for induction of apoptosis in senescent cells, serologic testing, and histologic examination. Serum samples can be obtained and submitted for serologic testing for antibody testing against a panel of lentiviral antigens. All animals may then be examined for gross lesions, and abnormal tissues can be fixed in formalin, embedded, sectioned at five-micron thickness, and stained with hematoxylin and eosin. Immunofluoresence and immunohistochemistry can be performed for p16 (to mark senescent cells) and caspase 8 (to mark apoptotic cells) on the sections. The level of apoptosis is compared between the two groups. It is contemplated that more apoptosis is observed in the senescent cells of the experimental group versus the control group.

It should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A composition comprising a conditionally replicating virus in a pharmaceutically compatible excipient, wherein the conditionally replicating virus has a recombinant genome construct in which a replication gene for the virus is placed under transcriptional control of a heterologous promoter,
   wherein the heterologous promoter is the p16 promoter,
   wherein when the conditionally replicating virus is applied to a mixed cell population comprising target cells that express p16, the p16 promoter causes the virus to replicate preferentially in the target cells, thereby causing lysis of the target cells and selectively depleting them from the cell population.

2. The composition of claim 1, wherein the genome construct of the conditionally replicating virus comprises more than one heterologous promoter.

3. The composition of claim 1, wherein the genome construct of the conditionally replicating virus comprises a replication gene for the virus placed under transcriptional control of a chemically inducible promoter.

4. The composition of claim 1, wherein replication of the virus is tissue specific.

5. The composition of claim 1, wherein the conditionally replicating virus is an adenovirus.

6. The composition of claim 1, wherein the conditionally replicating virus is a lentivirus, and the replication gene under transcriptional control of the p16 promoter is selected from gag, pol and env.

7. The composition of claim 1, wherein the nucleotide sequence of the p16 promoter comprises SEQ. ID NO:1.

8. The composition of claim 1, wherein the nucleotide sequence of the p16 promoter comprises SEQ. ID NO:2.

9. The composition of claim 1, wherein the genome of the conditionally replicating virus further comprises a caspase gene under transcriptional control of the p16 promoter.

10. A method of selectively depleting senescent cells from a mixed cell population or tissue, comprising combining the tissue with a composition according to claim 1 such that the conditionally replicating virus replicates in the senescent cells in the mixed cell population or tissue.

* * * * *

SEQUENCE LISTING

<160> NUMBER OF SEQ ID NOS: 3

<210> SEQ ID NO 1
<211> LENGTH: 1003
<212> TYPE: DNA
<213> ORGANISM: Homo sapiens

<400> SEQUENCE: 1

```
ctggtctttg gatcactgtg caactctgct tctagaacac tgagcacttt ttctggtcta      60
ggaattatga ctttgagaat ggagtccgtc cttccaatga ctccctcccc attttcctat     120
ctgcctacag gcagaattct cccccgtccg tattaaataa acctcatctt ttcagagtct     180
gctcttatac caggcaatgt acacgtctga gaaaccctttg ccccagacag ccgttttaca    240
cgcaggaggg gaaggggagg ggaaggagag agcagtccga ctctccaaaa ggaatccttt     300
gaactagggt ttctgactta gtgaaccccg cgctcctgaa aatcaagggt tgaggggta      360
gggggacact ttctagtcgt acaggtgatt tcgattctcg gtggggctct cacaactagg     420
aaagaatagt tttgcttttt cttatgatta aaagaagaag ccatactttc cctatgacac     480
caaacacccc gattcaattt ggcagttagg aaggttgtat cgcggaggaa ggaaacgggg     540
cggggggcgga tttcttttta acagagtgaa cgcactcaaa cacgcctttg ctggcaggcg    600
ggggagcgcg gctgggagca gggaggccgg agggcggtgt ggggggcagg tggggaggag    660
cccagtcctc cttccttgcc aacgctggct ctggcgaggg ctgcttccgg ctggtgcccc    720
cggggggagac ccaacctggg gcgacttcag gggtgccaca ttcgctaagt gctcggagtt    780
aatagcacct cctccgagca ctcgctcacg gcgtccccctt gcctggaaag ataccgcggt   840
ccctccagag gatttgaggg acaggtcgg aggggggctct tccgccagca ccggaggaag     900
aaagaggagg ggctggctgg tcaccagagg gtgggcgga ccgcgtgcgc tcggcggctg     960
cggagagggg gagagcaggc agcgggcggc ggggagcagc atg                     1003
```

<210> SEQ ID NO 2
<211> LENGTH: 2803
<212> TYPE: DNA
<213> ORGANISM: Mus sp.

<400> SEQUENCE: 2

```
ccattttatt tatttatta ttttattttt tagctgtaag cccaaggcag cagtttgcgg        60
tatttatata atgacatata gaagtaggta gaggatgtca gacaccctgc aaacatccaa     120
gtaggataca tctaacaacc aactccctag ccaaatctga catagatgcc ctatgaaaat     180
tagtgtaaag tcactgcttt tatagctaca tctgcataga tcccctgtat gaaagcatgt    240
actacctgga taataatatc tgtatttttc tgtagtagga aatcagtgta gttttaaaa     300
ccaaaaagta ttgttattaa tctatctttg atctcaaaca atttcaatga cctagtatag    360
tgatttctac ggaaagccct gcaatttact caaagcagtt tttaaatatt gttttaaaag    420
tgtgtgtgtg tgtgtgtgtg tgtgtgtgtg tgtgtggt gttaaagtca ttttcaaacc      480
cctcacaatg tcttgaatgt gacatttgag tcatttatgg taacttataa ctcctttgaa    540
gaagttattc agaattgagg ttccagacac acaaatgcac aatacaccat ttttccttcc    600
agttaacaat cagagggcaa cacttatttt taaaggaaaa tcgactccat aagggacttt    660
ataaagggt agacataaac cagtatcagg gataaactct ccgttcccct gtttaaccta     720
attttcccag ggccatcctg gaatacgaat tttctcttga aatacagtca agaaaaagt    780
ggtaggctac agagcagagg aaaacactgga cacagcgacc cacccccagag tcacttccct    840
taatctaatg actaggtttt ttctgaaagt tattttgtta gaacacagga acttttgcga    900
ccacagtgat gcttttagag ggttgaatcc tcaaaaagaa aattaatcgc aactagtaga    960
agggagatta cttattgatt cttataactt ctgcaggaat acacagttat gagttagggc   1020
```

```
aaagagaaaa ttgactttta atattctcta tcactaacat gagagaacat gtatgtgttc      1080
caaaataatt tttatttatt gaaaacccgc tatatacctg gattttcaca gaatattcat      1140
tactctccaa aatggccttt tctaggtgaa ttttattttc cttacagacc tcaagaagtt      1200
tacataattt acttaaacct gaggagagag aacaaagcct cagaaaattt acatagttta      1260
tttaaactaa actcagcttg cttggtagca gcttctaatc ccagcagtta aagagacaga      1320
agcagggcca acctgggta taatataagg tgagactctc cttctttct ctctgtctct        1380 gtctgtctct gtctctgtgt gtgtgtgtgt gtgtgtgtgt gtgtgtgtgt gtctcctctc      1440
tctctctctc tctctctctc tctctctctc tgtctctctc tccctccccc tccctccctc      1500
tccccctcct ctctccctcc ctctccctcc ccccccccca cacatttgaa ttcgtggagt      1560
tggtaaatga ggggtcagtt ctctgtctgt ctgtagtttt tgtccacag gatatgactg       1620 acattctcac cacacacata caaagtcaaa aatagctgtg gccatataaa gaatatgggg      1680
agagaaaatt attcaaaatc tgcagaaaat aatgccaggc ctttaatcct ggcacccagg      1740
aggcagaagg gagacagagt tctgagttta tgctgagttc caggagtgga agaaagggcc      1800
attgcctttc tggtgaggac tgtcttttta aatcctccct tctgtccagt actggtaact      1860
ctgcccaaag cgtgttcttc ttcctgcctc acaagattgc aaagacgttt ttaacgaaca      1920
atttaaaccg gtgcaacgtt tatgcgcagc acaccaactc atttaaacaa acaacagccc      1980
cataaaatag aaatacttta taagcagatt gccctccgat gacttcaccc cgtcactttt      2040
ttatagttgt gtacagaatc ctagcactga tacagcaaca tcagaaatgt ttctgcaaat      2100
ccttcgcaaa gattcggatt tcatactggg cgtggtaccc tccaaaatga gttgtttgag      2160
ctagggttgt tgggatctca gcttggcgaa gttgtagctc tttcttctga ataaaagatg      2220
acacaatttt ctgctaagat gttaaatacc ttaagtttca gtgtagtgat gaaaattacc      2280
ctccttcgtt tttctaatac ctgggtgttg cactggggag gaaggagaga tttcgagaag      2340
gactagttca ctttctcaga agacacgtgt gcacttcttt gctgtgcggg tccagaagga      2400
gcccagcgtg tcaaagggtg accaggcatg ggggaggggt gttagcgtgg gtagcaggcg      2460
ggggctgtcc gatcctttag cgctgtttca acgcccagct ctcctcctga accctgcatc      2520
tcttctgtag tccgggctcc atcccttttcc cctcccccat ccggaggtgg gggaacagc      2580 agtgttttca ggggtgttca attcatgcta tattcagggc aaatagcgcc acctatggcg      2640
ggctgtggag ccaggtcagg agcagagtgt ggctccccccc cccccccaca ccatcctcag      2700
aggaaggaag gagggaccca ctggtcacac gactgggcga ttgggcgggc actgaatctc      2760
cgcgaggaaa gcgaactcga ggagagccat ctggagcagc atg                       2803

<210> SEQ ID NO 3
<211> LENGTH: 1395
<212> TYPE: DNA
<213> ORGANISM: Homo sapiens

<400> SEQUENCE: 3
atggacttca gcagaaatct ttatgatatt ggggaacaac tggacagtga agatctggcc        60
tccctcaagt tcctgagcct ggactacatt ccgcaaagga agcaagaacc catcaaggat       120
gccttgatgt tattccagag actccaggaa aagagaatgt tggaggaaag caatctgtcc       180
ttcctgaagg agctgctctt ccgaattaat agactggatt tgctgattac ctacctaaac       240
actgaaaagg aggagatgga aagggaactt cagacaccag gcagggctca aatttctgcc       300
tacagggtca tgctctatca gatttcagaa gaagtgagca gatcagaatt gaggtctttt       360
```

```
aagtttcttt tgcaagagga aatctccaaa tgcaaactgg atgatgacat gaacctgctg    420
gatattttca tagagatgga gaagagggtc atcctgggag aaggaaagtt ggacatcctg    480
aaaagagtct gtgcccaaat caacaagagc ctgctgaaga taatcaacga ctatgaagaa    540
ttcagcaaag gggaggagtt gtgtggggta atgacaatct cggactctcc aagagaacag    600
gatagtgaat cacagacttt ggacaaagtt taccaaatga aaagcaaacc tcggggatac    660
tgtctgatca tcaacaatca caattttgca aaagcacggg agaaagtgcc caaacttcac    720
agcattaggg acaggaatgg aacacacttg gatgcagggg ctttgaccac gacctttgaa    780
gagcttcatt ttgagatcaa gccccacgat gactgcacag tagagcaaat ctatgagatt    840
ttgaaaatct accaactcat ggaccacagt aacatggact gcttcatctg ctgtatcctc    900
tcccatggag acaagggcat catctatggc actgatggac aggaggcccc catctatgag    960
ctgacatctc agttcactgg tttgaagtgc ccttcccttg ctggaaaacc caaagtgttt   1020
tttattcagg cttgtcaggg ggataactac cagaaaggta tacctgttga gactgattca   1080
gaggagcaac cctatttaga aatggattta tcatcacctc aaacgagata tatcccggat   1140
gaggctgact ttctgctggg gatggccact gtgaataact gtgtttccta ccgaaaccct   1200
gcagagggaa cctggtacat ccagtcactt tgccagagcc tgagagagcg atgtcctcga   1260
ggcgatgata ttctcaccat cctgactgaa gtgaactatg aagtaagcaa caaggatgac   1320
aagaaaaaca tggggaaaca gatgcctcag cctactttca cactaagaaa aaaacttgtc   1380
ttcccttctg attga                                                    1395
```